United States Patent [19]

Myers

[11] Patent Number: 5,183,920

[45] Date of Patent: Feb. 2, 1993

[54] INTEGRATED PROCESS FOR THE PRODUCTION OF DIMETHYL CARBONATE

[75] Inventor: Harold D. Myers, Midland, Mich.

[73] Assignee: The Dow Chemical Company, Midland, Mich.

[21] Appl. No.: 819,895

[22] Filed: Jan. 13, 1992

[51] Int. Cl.$^5$ .................... C07C 68/00; C07C 69/96
[52] U.S. Cl. .................................................. 558/277
[58] Field of Search ........................................ 558/277

[56] References Cited

U.S. PATENT DOCUMENTS

| | | | |
|---|---|---|---|
| 4,318,862 | 3/1982 | Romano | 260/463 |
| 4,360,477 | 11/1982 | Hallgren et al. | 558/277 |
| 4,370,275 | 1/1983 | Stammann et al. | 558/277 |
| 4,644,078 | 2/1987 | Morris et al. | 558/277 |
| 4,689,430 | 8/1987 | Morris et al. | 558/277 |
| 4,762,858 | 8/1988 | Hucul et al. | 518/714 |
| 4,785,130 | 11/1985 | Bhattacharya | 558/277 |
| 5,004,827 | 4/1991 | Curnutt | 558/277 |
| 5,093,513 | 3/1992 | Sawicki et al. | 558/277 |

FOREIGN PATENT DOCUMENTS

| | | | |
|---|---|---|---|
| 0134668 | 3/1985 | European Pat. Off. | 558/277 |
| 3926709 | 2/1991 | Fed. Rep. of Germany | 558/277 |

OTHER PUBLICATIONS

Pasquon, I. Latin American Applied Research 20, 15-24 (1990).

*Primary Examiner*—Floyd D. Higel

[57] ABSTRACT

An integrated process for the production of dimethyl carbonate is disclosed. The processes utilizes oxygen and an inexpensive carbon source such as natural gas as reactants. Other reactants are generated within the process and used without isolation. The process produces dimethyl carbonate and water with other by-products being recycled.

11 Claims, 1 Drawing Sheet

INTEGRATED PROCESS FOR THE PRODUCTION OF DIMETHYL CARBONATE

BACKGROUND OF THE INVENTION

The present invention relates to a continuous process for the production of dimethyl carbonate.

The addition of dimethyl carbonate to gasoline as an oxygenate as an alternative to methyl t-butyl ether is being explored. This is generating interest in methods of production of dimethyl carbonate. Currently, it is known to prepare dimethyl carbonate by the oxidative carbonylation of methanol using palladium or copper halide catalysts in both liquid and vapor phase processes. However, existing methods are not likely to produce dimethyl carbonate economically in the quantities which would be needed for its use as a gasoline additive. Therefore, improved methods for the manufacture of dimethyl carbonate are needed.

SUMMARY OF THE INVENTION

The present invention is an integrated, process for the production of dimethyl carbonate from a carbon source, oxygen and optionally, carbon dioxide, comprising the steps of
(a) reacting a carbon source, oxygen and, optionally, carbon dioxide to form a synthesis gas comprising carbon monoxide and hydrogen:
(b) reacting the synthesis gas formed in step (a) to produce methanol with excess carbon monoxide:
(c) reacting the methanol and carbon monoxide formed in step (b) with oxygen in the presence of a catalyst to form predominantly dimethyl carbonate and water:
(d) separating the products, unreacted reactants and any by-products formed in steps (a), (b) and (c); and
(e) recycling any unreacted reactants and any by-products formed in steps (a), (b) or (c) to step (a) or (c) as appropriate.

The integrated process is conducted without the need to isolate any of the intermediate products, i.e., the hydrogen, the carbon monoxide or the methanol. Any by-products formed in steps (a), (b) and (c) are carried through and separated from the products in step (d). With the exception of water, essentially all of the by-products and unreacted reactants are recycled to the appropriate step. For example, unreacted methanol, carbon monoxide, oxygen and inerts, are recycled to the dimethyl carbonate reaction. Other by-products from the dimethyl carbonate reaction are recycled to the synthesis gas step. Since the process involves continuous recycling and has the capability to recycle by-products, overall efficiencies are very high with selectivities based on both oxygen and the carbon source approaching 100 percent.

This process is advantageous in that it uses inexpensive and readily available raw materials, avoids the need to isolate and/or transport methanol and has the capability of recycling any by-products produced so that the end products are essentially only water and dimethyl carbonate. Additionally, the total capital requirements are reduced in an integrated process due to the use of common equipment for processing.

DETAILED DESCRIPTION OF THE ILLUSTRATIVE EMBODIMENTS

Figure 1:
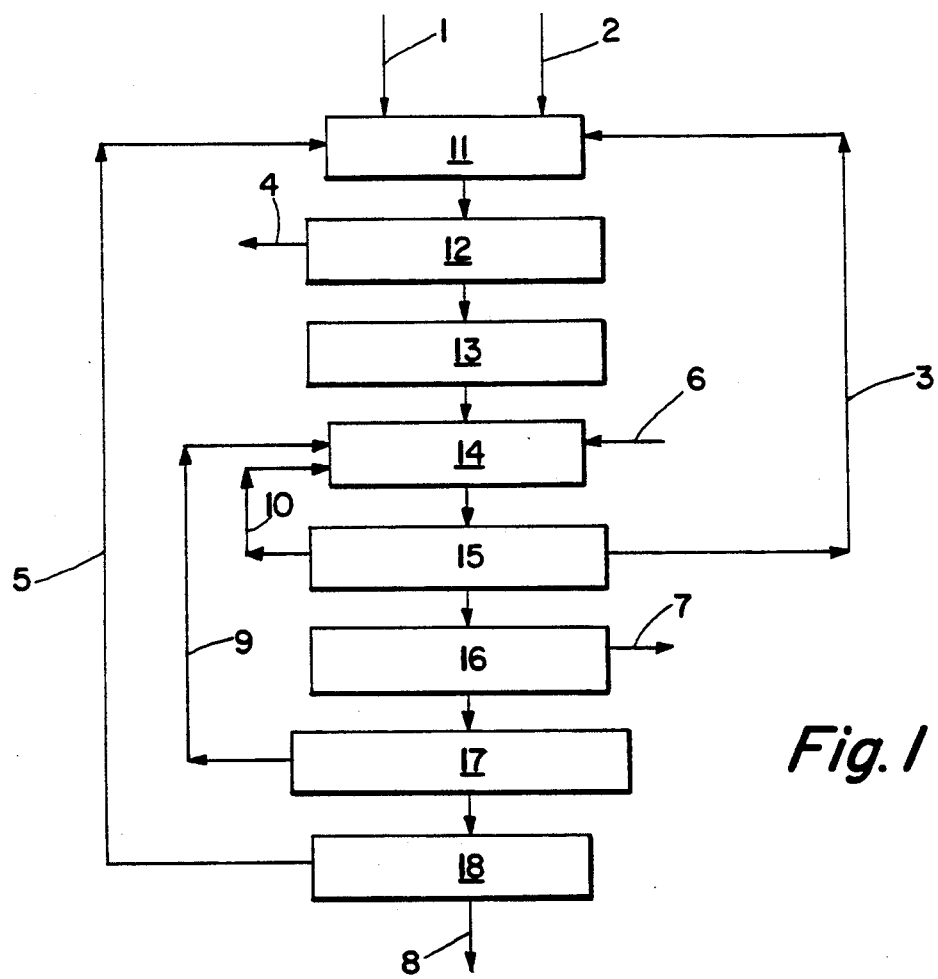

This integrated process for the production of dimethyl carbonate encompasses the following reactions:

$$3CH_4 + 1.5O_2 \rightarrow 3CO + 6H_2 \tag{I}$$

$$2H_2 + O_2 \rightarrow 2H_2O \tag{II}$$

$$3CO + 4H_2 \rightarrow 2CH_3OH + CO \tag{III}$$

$$2CH_3OH + CO + 0.5O_2 \rightarrow (CH_3O)_2CO + H_2O \tag{IV}$$

The net reaction can be expressed as $$3CH_4 + 3O_2 \rightarrow (CH_3O)_2CO + 3H_2O \tag{V}$$

showing that the total process involves the reaction of a carbon source and oxygen to produce dimethyl carbonate and water.

Steps (a) and (b) of the process, which encompass Reactions I, II and III, are generally known. See, for example, the discussions in Kirk-Othmer Encyclopedia of Chemical Technology, 3rd Edition, Vol. 15, 400–409 (John Wiley and Sons, 1981) pertaining to methanol production and the discussion by Reed, C. L. and Kuhre, C. J. in "Make Syngas by Partial Oxidation," *Hydrocarbon Processing*, Vol. 58, No. 9, Sept. 1979, 191–194.

Carbon dioxide is used in step (a) when necessary to obtain the desired synthesis gas ratio for methanol production. Typically, a carbon source is reacted with steam in steam reforming reactions or, preferably with oxygen and steam in partial oxidations. The partial oxidation reaction facilitates the recycle of any by-products formed. Additionally, the use of oxygen in both step (a) and step (c) permits economies of scale in the use of oxygen.

The syngas produced contains carbon monoxide and hydrogen with minor amounts of water, carbon dioxide and inert materials such as nitrogen. If desired, the process can be modified to extract a portion of the hydrogen produced by commonly used extraction technologies such as pressure swing adsorption or separation membranes. The carbon source is any suitable carbon rich substance such as natural gas, refinery off gas, methane, naphtha, heavy petroleum oils and coal. If necessary, the carbon source is desulfurized prior to use in the formation of the synthesis gas.

The ratios of reactants to form the synthesis gas are selected to result in a product containing hydrogen and carbon monoxide in the needed ratio for the synthesis of methanol. Methanol is produced by one or both of the following reactions:

$$CO + 2H_2 \rightleftharpoons CH_3OH$$

$$CO_2 + 3H_2 \rightleftharpoons CH_3OH + H_2O$$

The carbon monoxide reaction is the predominant reaction by which methanol is produced. The use of a slight stoichiometric excess of carbon monoxide is preferred. The molar ratio of hydrogen to carbon monoxide preferably ranges from 3:1 to 1:1, more preferably from 3:1 to 1.1:1 and is most preferably from about 1.2:1 to 1.5:1. A particularly preferred ratio is about 1.3:1. By maintaining only a slight stoichiometric excess of carbon monoxide, the reaction is driven toward methanol production and excess carbon monoxide is available for the dimethyl carbonate reaction. This is in contrast to typical methanol synthesis where a 2:1 ratio of hydrogen to carbon monoxide is typically used.

The synthesis gas is converted to methanol in step (b) using conventional techniques either in vapor or liquid phase. For example, it is well known than methanol can be produced from carbon monoxide and hydrogen in the presence of a metal catalyst. Older high pressure (25 to 35 MPa or 250 to 350 atmospheres) processes use, for example, a zinc oxide/chromium oxide catalyst. It is preferred to use a more modern, low pressure (5 to 25 MPa or 50 to 250 atmospheres) process using a catalyst such as copper/zinc oxide/alumina. An advantage of the integrated process is the use of lower hydrogen/carbon monoxide ratios than in conventional methanol synthesis.

The methanol produced in step (b), without isolation from any by-products or unused reactants, is used as a reactant in step (c) for the production of dimethyl carbonate. The dimethyl carbonate can be produced by known processes. For example, it may be produced by the method described in U.S. Pat. No. 5,004,827. In this process, methanol, oxygen and carbon monoxide are reacted in the vapor phase in the presence of a heterogeneous catalyst containing a supported metal halide such as copper chloride. Additionally, mixed metal halides such as copper chloride/potassium chloride are useful in the catalyst. Another useful catalyst is copper halide with a tertiary organophosphorus compound. The use of this latter catalyst is discussed in PCT patent application, number WO 9015791. Other processes for the production of dimethyl carbonate are discussed in U.S. Pat. No. 3,980,690 to Cipriani et al. The identity of the catalyst and precise reaction conditions are not critical to the practice of the integrated process.

In general, the carbonylation involves contacting carbon monoxide, oxygen and methanol in the vapor phase and passing them over a suitable catalyst. The molar ratio of carbon monoxide to methanol may be any which results in preparation of dimethyl carbonate and is preferably between 0.1:1 and 1000:1, more preferably between 0.3:1 and 100:1 and most preferably between 0.4:1 and 5:1. The molar ratio of oxygen to methanol may be any which results in preparation of dimethyl carbonate and is preferably between 0.1:1 and 1000:1, more preferably between 0.2:1 and 100:1 and most preferably between 0.25:1 and 5:1. The molar ratio of oxygen to carbon monoxide may be any which results in preparation of dimethyl carbonate and is preferably between 0.05:1 and 1000:1, more preferably between 0.1:1 and 100:1 and most preferably between 0.2:1 and 5:1.

The production of dimethyl carbonate can be performed at any temperature and pressure at which the reaction proceeds. Preferred temperatures are between about 20° C. and 175° C., with between 90° C. and 150° C. being more preferred and between 115° C. and 150° C. being most preferred. The pressure can be atmospheric or superatmospheric with preferred pressures being between 1 and 100 atmospheres. More preferred pressures are between 15 and 25 atmospheres. As is recognized by those skilled in the art, in any reaction involving oxygen, diluents are used to avoid flammability issues.

Representative of the products of the dimethyl carbonate reaction are dimethyl carbonate, and, as by-products, water, methyl acetate, methylal, methyl formate and carbon dioxide. The exact identity of the by-products varies based on, for example, the reaction conditions and catalyst used. The dimethyl carbonate is purified by known methods such as distillation and recovered using known techniques. The by-products, such as methyl acetate, methyl formate, methylal and carbon dioxide, and any unused reactants are separated using known techniques and are reclaimed or recycled to the appropriate steps in the integrated process. For example, various hydrocarbons such as methylal, methyl formate and methyl acetate can be recycled to the first step to be used as carbon sources in the synthesis gas reaction. Similarly, carbon dioxide is recycled to the partial oxidation process while oxygen and excess carbon monoxide are recycled to the dimethyl carbonate production step.

One embodiment of the integrated process is shown schematically in FIG. 1. A methane stream 1 and an oxygen stream 2 along with a recycled hydrocarbon by-product stream 5 and a carbon dioxide stream 3 are fed to a syngas reactor 11 and reacted to form synthesis gas. Water is separated from the syngas produced in a water separator 12 and is removed from the syngas via stream 4. The syngas is then fed to the methanol reactor 13. Methanol is formed and is fed, without isolation from unreacted carbon monoxide or purification, to the dimethyl carbonate reactor 14. Additional oxygen (via stream 6) is fed to the dimethyl carbonate reactor 14. Also, recycled methanol (stream 9) and recycled inerts (stream 10) are fed to the dimethyl carbonate reactor 14. Carbon dioxide is separated from the dimethyl carbonate product and recycled to the syngas reaction via stream 3. Water is separated in separator 16 and removed from the dimethyl carbonate product via stream 7. Unreacted methanol is separated in separator 17 and recycled to the dimethyl carbonate reactor 14 via stream 9. Inert gases such as nitrogen are also separated from the dimethyl carbonate product and recycled to the dimethyl carbonate reactor 14 via stream 10. The dimethyl carbonate is purified and recovered from stream 8 after being separated from by-products which are recycled to the syngas reactor 11 via stream 5.

The following example and comparative example are provide to illustrate the invention and should not be viewed as limiting it in any way.

EXAMPLE

Integrated Process for Production of Dimethyl Carbonate (See FIG. 1)

Natural gas via stream 1 (66,585 lb/hr) is desulferized, compressed and mixed with carbon dioxide via stream 3 (48,750 lb/hr) which is recycled from the dimethyl carbonate reactor 14. This is fed along with oxygen via stream 2 (81,147 lb/hr) to a syngas reactor 11 where synthesis gas (syngas) is prepared by partial oxidation. The syngas product is then subjected to a water separation at 300° C. and 35 atmospheres in water separator 12. The separated water (33,232 lb/hr) is removed from the system via stream 4 or returned to the syngas reactor 11 as necessary.

The syngas is compressed and fed to the methanol reactor 13 wherein the carbon monoxide and hydrogen is contacted in the presence of a copper/zinc oxide/alumina catalyst and methanol is formed at 300° C. and 100 atmospheres.

The product and unreacted reactants from the methanol reaction plus 51,663 lb/hr oxygen via stream 6 and 472,853 lb/hr methanol via stream 9 recycled from the methanol separation system 17 are fed to the dimethyl carbonate reactor 14 where they are contacted in the presence of a copper chloride on carbon catalyst and dimethyl carbonate is formed at 120° C. and 20 atmospheres. The reaction produces 124,623 lb/hr dimethyl carbonate that is removed from the system after purification via stream 8 and 41,540 lb/hr water which is separated in water separator 16 and removed from the system via stream 7. By-products produced are methyl acetate and methylal (13,665 lb/hr), methyl formate (11,078 lb/hr) which are separated from the dimethyl carbonate in a purification system 18 and recycled to the syngas reactor 11 via stream 5. Oxygen (147,098 lb/hr), carbon monoxide (232,759 lb/hr) and inerts (1,189,000 lb/hr) are separated in a gas separation system 15 and stream 10 is recycled back to the dimethyl carbonate reactor 14. Carbon dioxide (48,750 lb/hr) is recycled via stream 3 to syngas reactor 11.

The overall selectivity (product of conversion of reactant and yield of dimethyl carbonate) of this integrated process is essentially 100 percent based on the oxygen and methane used as starting materials.

COMPARATIVE EXAMPLE

Figure 2:
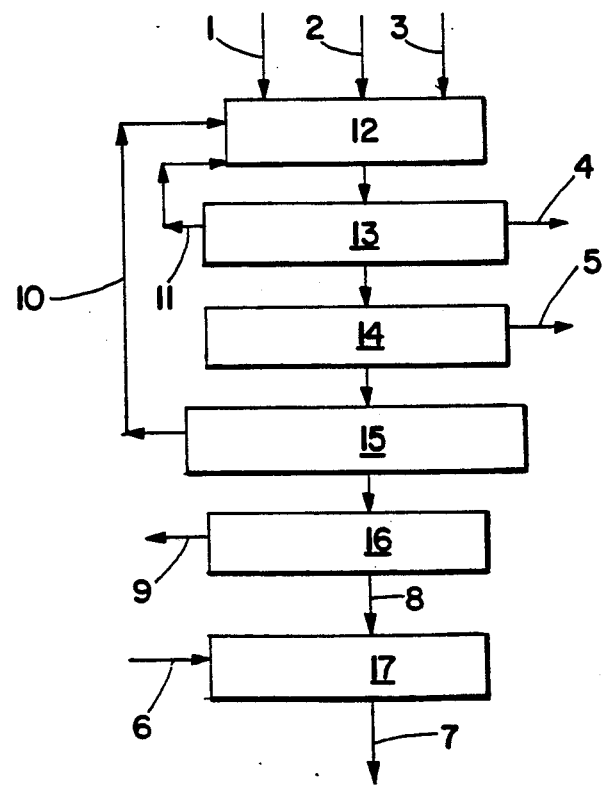

Non-integrated Process for the Production of Dimethyl Carbonate (see FIG. 2)

In this example, methanol (118,213 lb/hr) via stream 3, oxygen (51,663 lb/hr) via stream 2 and carbon monoxide (69,779 lb/hr) via stream 1 are contacted in the presence of a copper chloride on carbon catalyst (same as the catalyst in the Example) to form dimethyl carbonate in the dimethyl carbonate reactor 12. The product of this reaction is fed to a gas separation system 13 where carbon dioxide (48,750 lb/hr), carbon monoxide (232,759 lb/hr), oxygen (147,098 lb/hr) and nitrogen (1,189,000 lb/hr) are separated from the other products and by-products of the dimethyl carbonate reaction. The carbon dioxide is removed via stream 4 and the carbon monoxide, oxygen and nitrogen are recycled to the dimethyl carbonate reactor 12 via stream 11. The remaining products are fed to water separator 14 where water (41,540 lb/hr) is removed via stream 5. Following the water removal, the reactant stream is fed to a methanol separator 15 and the separated methanol (472,853 lb/hr) is recycled to the dimethyl carbonate reactor 12 via stream 10. The remaining dimethyl carbonate and by-products are fed to a purification system 16. Here, dimethyl carbonate (124,623 lb/hr) is recovered via stream 9. The remaining by-products, methylal, methyl formate and methyl acetate (24,743 lb/hr) along with air via stream 6 are fed to burner 17 and flue gas is produced via stream 7.

The selectivity based on carbon monoxide is 55 percent. The selectivity based on methanol is 75 percent. The selectivity based on oxygen is 43 percent.

A comparison of the selectivity or efficiency of the Example and the Comparative Example clearly demonstrates the advantages of the process of this invention as shown in the Table below.

| RAW MATERIAL EFFICIENCIES | | |
|---|---|---|
| Feedstock | Integrated Process | Single Stage Process |
| Methane | 100% | — |
| Oxygen | 100% | 43% |
| Carbon Monoxide | — | 56% |

| RAW MATERIAL EFFICIENCIES | | |
|---|---|---|
| Feedstock | Integrated Process | Single Stage Process |
| Methanol | — | 75% |

What is claimed is:

1. An integrated process for the production of dimethyl carbonate from a carbon source suitable for the production of synthesis gas and oxygen comprising the steps of
   (a) reacting the carbon source and oxygen to form a synthesis gas comprising hydrogen and carbon monoxide in a molar ratio of from 1:1 to 3:1;
   (b) reacting the carbon monoxide and hydrogen formed in step (a) to produce methanol with excess carbon monoxide;
   (c) reacting the methanol and carbon monoxide formed in step (b) with oxygen in the presence of a catalyst to form predominantly dimethyl carbonate and water;
   (d) separating the products, any unreacted reactants and any by-products formed in steps (a), (b) and (c); and
   (e) recycling any by-products formed in steps (a), (b) or (c) and any unreacted reactants.

2. The process of claim 1 wherein the carbon source is natural gas.

3. The process of claim 1 wherein the by-products formed in step (c) and separated in step (d) are recycled to step (a).

4. The process of claim 1 wherein the catalyst used is a heterogeneous catalyst containing copper impregnated on activated carbon.

5. The process of claim 1 wherein the synthesis gas produced in step (a) contains hydrogen and carbon monoxide in a molar ratio of from 1.1:1 to 3:1.

6. The process of claim 1 wherein the synthesis gas produced in step (a) contains hydrogen and carbon monoxide in a molar ratio of from 1.2:1 to 1.5:1.

7. An integrated process for the production of dimethyl carbonate from a carbon source suitable for the production of synthesis gas, oxygen and carbon dioxide, comprising the steps of
   (a) reacting the carbon source, oxygen and carbon dioxide to form a synthesis gas comprising hydrogen and carbon monoxide in a molar ratio of from 1:1 to 3:1;
   (b) reacting the carbon monoxide and hydrogen formed in step (a) to produce methanol with excess carbon monoxide;
   (c) reacting the methanol and carbon monoxide formed in step (b) with oxygen in the presence of a catalyst to form predominantly dimethyl carbonate and water;
   (d) separating the products, any unreacted reactants and any by-products formed in steps (a), (b) and (c); and
   (e) recycling any by-products formed in steps (a), (b) or (c) and any unreacted reactants.

8. The process of claim 7 wherein the synthesis gas produced in step (a) contains hydrogen and carbon monoxide in a molar ratio of from 1.1:1 to 3:1.

9. The process of claim 7 wherein the synthesis gas produced in step (a) contains hydrogen and carbon monoxide in a molar ratio of from 1.2:1 to 1.5:1.

10. The process of claim 7 wherein the carbon source is natural gas.

11. The process of claim 7 wherein the by-products formed in step (c) and separated in step (d) are recycled to step (a).

* * * * *